United States Patent [19]

Breunig

[11] Patent Number: 5,078,993
[45] Date of Patent: Jan. 7, 1992

[54] OINTMENT PHARMACEUTICAL FORMULATION

[75] Inventor: Charles F. Breunig, Greenville, N.Y.
[73] Assignee: Stiefel Laboratories, Inc., Coral Gables, Fla.
[21] Appl. No.: 451,881
[22] Filed: Dec. 18, 1989
[51] Int. Cl.$^5$ .............. A61K 31/74; 424 78; 424 59
[52] U.S. Cl. .............................. 514/772.4
[58] Field of Search ................... 424/78, 59
[56] References Cited

U.S. PATENT DOCUMENTS

| 4,293,544 | 10/1981 | Elrni ........................ 424/59 |
| 4,322,545 | 3/1982 | Lrala, Jr. ................... 424/59 |
| 4,323,694 | 4/1982 | Srala, Jr. ................... 424/59 |

FOREIGN PATENT DOCUMENTS 615014 1/1984 Japan.

Primary Examiner—Thurman K. Page
Assistant Examiner—Peter F. Kulkosky
Attorney, Agent, or Firm—Matthews, Woodbridge and Collins

[57] ABSTRACT

An ointment-like base comprises a blend of at least one topically acceptable alkyl ester of an aromatic carboxylic acid and at least one topically acceptable dialkyl ester of a hydroxyalkanedicarboxylic acid, the ratio of the two esters being from about 1:3 to 4:1. This blend is combined with from about 10 to about 30% of a polysiloxane and from about 5 to about 20% of a topically acceptable alkanol having 10 to 20 carbon atoms.

17 Claims, No Drawings

OINTMENT PHARMACEUTICAL FORMULATION

The present invention pertains to a base for a topical pharmaceutical composition having ointment properties, and to the compositions prepared from that base.

Although the definition will vary, ointments generally are relatively thick topical preparations which employ hydrocarbon substances such as petrolatum or mixtures thereof with mineral oil as the formulation base. They are used as a vehicle for a variety of topically active pharmaceutical agents. Often the ointment is rubbed into the skin, becoming somewhat more fluid in the process as its temperature is raised in contact with the body. The formulation provides lubrication and a degree of protection but also has a somewhat "greasy" feel which is unpleasant to some patients. Moreover, the hydrocarbon nature of the base discourages some physicians from prescribing products using these formulations in some conditions (notably acne).

Non-hydrocarbon ointment bases have been proposed to avoid these problems. These include materials such as polyethylene glycol, or mixtures thereof, which provides a water-soluble ointment base, and castor oil but these apparently have not found wide acceptance.

The present invention pertains to a base for preparing a topical formulation which has ointment-like properties but which is more cosmetically elegant and desirably not based on a hydrocarbon vehicle.

In particular, the base comprises (i) a blend of at least one topically acceptable alkyl ester of an aromatic carboxylic acid and at least one topically acceptable dialkyl ester of a hydroxyalkanedicarboxylic acid; (ii) a polysiloxane emollient; and (iii) a topically acceptable alkanol emollient having 10 to 20 carbon atoms.

Referring first to the blend of esters, the first component will be an alkyl ester of an aromatic carboxylic acid. Typically the aromatic carboxylic acid is benzoic acid and the alkyl ester is derived from straight or branched alkanols having 10 to 20 carbon atoms. Representative examples include lauryl benzoate, palmyl benzoate, stearyl benzoate, isostearyl benzoate, and the like. Mixtures of two or more alkyl esters of aromatic carboxylic acids can be used.

The second component of the blend of esters is one or more dialkyl ester of a hydroxyalkanedi- or tricarboxylic acid in which each alkyl group is straight or branched and has from 6 to 12 carbon atoms; e.g., a dialkyl ester of malic, citric, tartronic, or tartaric acids such as dioctyl malate, bis(2-ethylhexyl) malate, and the like.

The weight ratio of the first component, the alkyl ester of the aromatic carboxylic acid, to the second, the dialkyl ester, will be in the range from about 1:3 to 4:1. While a base can be prepared using only the alkyl ester or only the dialkyl ester of the hydroxycarboxylic acid, superior results are obtained from a blend of the two components. Preferably the two are present in about equal amount, the ratio of alkyl ester to dialkyl ester being about 1:1. The preferred alkyl ester of the aromatic carboxylic acid is stearyl benzoate, particularly isostearyl benzoate, whereas the preferred dialkyl ester is dioctyl malate, particularly bis(2-ethylhexyl) malate.

In addition, the base will contain one or more emollient as herein defined.

The first emollient is from about 10 to about 30%, based on the weight of the blend, of a polysiloxane. The polysiloxane can be for example dimethicone or cyclomethicone, and preferably is present in an amount of from 10 to 25%, again based on the weight of the blend of esters.

The second emollient is from about 5 to about 20%, based on the weight of the ester blend, of a topically acceptable alkanol having 10 to 20 carbon atoms. The alcohol can be the same as or different from that from which the alkyl ester of the aromatic carboxylic acid is derived, as for example dodecanol (lauryl alcohol) tetradecanol, hexadecanol (stearyl alcohol), octadecanol, branched isomers thereof such as isostearyl alcohol, and the like. Preferred is stearyl alcohol. Generally the alcohol will be present in an amount of about 10%, again based on the weight of blend of esters.

The foregoing ingredients are mixed to produce the ointment base. A final pharmaceutical composition having ointment-like properties then is prepared by combining this base with at least one thickener in an amount of from about 15% to about 70%, preferably about 50%, of the amount of the base. In a final composition, the alkyl ester of the aromatic carboxylic acid thus will be present in an amount of from about 15 to about 60% while the dialkyl ester will be present in an amount of from about 15 to about 45% of the overall composition. The precise amount of thickener added will depend on the viscosity of the blend of esters and the final consistency which is desired.

Generally the thickener is one or more polysaccharides and/or ethylene-vinylacetate copolymers. The polysaccharides can be any of the materials of this class heretofore used in pharmaceutical preparations such as starch, or cellulose derivatives. Preferably the thickener is a combination of several materials such as starch, cellulose, and ethylene/vinyl acetate copolymer.

Conventional preservatives such as propylparaben and butylparaben can be added in effective amounts, as can fragrances and dyes.

The resultant formulation is suitable for a wide variety of therapeutic agents such as anti-inflammatory agents, antifungal agents, antibiotics, anesthetics, etc., which are administered for their known indications. Advantageously, the final ointment is stable, does not have a greasy feel, and appears to enjoy user preference when compared to conventional hydrocarbon-based ointments.

The following example will serve to further typify the nature of the invention but should not be construed as a limitation on the scope there which is defined solely by the appended claims.

EXAMPLE

The following ingredients are thoroughly blended:

| Ingredient | Parts by Weight |
| --- | --- |
| Base: | |
| Isostearyl Benzoate | 23.75 |
| bis(2-Ethylhexyl) Malate | 23.85 |
| Cyclomethicone | 10.00 |
| Stearyl Alcohol | 5.00 |
| Total | 62.60 |

These are combined with the following to produce the ointment-like composition:

| Thickener: | |
| --- | --- |

| -continued | |
|---|---|
| Starch | 10.00 |
| Microporous Cellulose | 10.00 |
| Ethylene/vinyl acetate copolymer | 15.00 |
| Total | 35.00 |
| Auxiliaries: | |
| Propylparaben | 0.10 |
| Butylparaben | 0.10 |
| Fragrance | 0.10 |
| Total | 0.30 |
| Active Ingredient: | |
| Erythromycin USP | 2.10 |
| Total for Composition | 100.00 |

The resulting ointment composition is off-white with a slight grainy appearance. It remains stable after standing for six months at ambient temperature and relative humidity.

What is claimed is:

1. A nonhydrocarbon base for a substantially nonaqueous topical pharmaceutical composition having stable, non-greasy, ointment properties, said base comprising:
   (a) a blend of (i) at least one topically acceptable alkyl ester of an aromatic carboxylic acid and (ii) at least one topically acceptable dialkyl ester of a hydroxyalkanedicarboxylic acid, the ratio of said alkyl ester to said dialkyl ester being from about 1:3 to 4:1;
   (b) from about 10 to about 30%, based on the weight of said blend, of a polysiloxane; and
   (c) from about 5 to about 20%, based on the weight of said blend, of a topically acceptable alkanol having 10 to 20 carbon atoms.

2. A base according to claim 1 wherein the alkyl ester of the aromatic carboxylic acid is the benzoate of a straight or branched alkanol having 10 to 20 carbon atoms.

3. A base according to claim 1 wherein the dialkyl ester of a hydroxyalkanedicarboxylic acid is a dialkyl malate or dialkyl citrate in which each alkyl group is straight or branched and has from 6 to 12 carbon atoms.

4. A base according to claim 1 wherein the ratio of alkyl ester to dialkyl ester is about 1:1.

5. A base according to claim 1 wherein the alkyl ester is a stearyl benzoate.

6. A base according to claim 5 wherein the stearyl benzoate is isostearyl benzoate.

7. A base according to claim 1 wherein the dialkyl ester is dioctyl malate.

8. A base according to claim 7 wherein the dioctyl malate is bis(2-ethylhexyl) malate.

9. A base according to claim 1 wherein the alkanol is stearyl alcohol.

10. A base according to claim 9 wherein the stearyl alcohol is present in an amount of about 10%, based on the weight of said blend.

11. A base according to claim 9 wherein the polysiloxane is cyclomethicone.

12. A base according to claim 11 wherein the cyclomethicone is present in an amount of from 10 to 25%, based on the weight of said blend.

13. A topical substantially nonaqueous pharmaceutical composition having stable, non-greasy ointment properties comprising a nonhydrocarbon base according to claim 1 admixed with up to about 50% of at least one thickener.

14. A topical pharmaceutical composition according to claim 13 wherein the thickener is one or more members selected from the group consisting of polysaccharides and ethylenevinylacetate copolymers.

15. A topical pharmaceutical composition according to claim 13 wherein the thickener is present in an amount of from about 15% to about 50% of the amount of said base.

16. A topical pharmaceutical composition according to claim 15 wherein the thickener is present in an amount of about 50% of the amount of said base.

17. A topical pharmaceutical composition according to claim 15 wherein the thickeners are a mixture of starch, cellulose, and ethylene/vinyl acetate copolymer.

* * * * *